United States Patent
Decherf et al.

(10) Patent No.: US 10,675,133 B2
(45) Date of Patent: Jun. 9, 2020

(54) DEVICE FOR THE ATRAUMATIC TRANSFER OF A MATERIAL OR SUBSTANCE WITH A REPRODUCTIVE, THERAPEUTIC OR DIAGNOSTIC PURPOSE INTO FEMALE MAMMALS

(71) Applicant: ELEXINN, Migennes (FR)

(72) Inventors: Agathe Decherf, Migennes (FR); Pierrick Drevillon, Migennes (FR)

(73) Assignee: ELEXINN, Migennes (FR)

( * ) Notice: Subject to any disclaimer, the term of this patent is extended or adjusted under 35 U.S.C. 154(b) by 366 days.

(21) Appl. No.: 15/315,975

(22) PCT Filed: Jun. 3, 2015

(86) PCT No.: PCT/FR2015/051474
§ 371 (c)(1),
(2) Date: Dec. 2, 2016

(87) PCT Pub. No.: WO2015/185863
PCT Pub. Date: Dec. 10, 2015

(65) Prior Publication Data
US 2017/0119513 A1    May 4, 2017

(30) Foreign Application Priority Data
Jun. 4, 2014    (FR) ...................................... 14 55079

(51) Int. Cl.
*A61D 19/02*    (2006.01)
*A61B 17/43*    (2006.01)
(Continued)

(52) U.S. Cl.
CPC .......... *A61D 19/027* (2013.01); *A61B 5/4325* (2013.01); *A61B 17/43* (2013.01);
(Continued)

(58) Field of Classification Search
CPC .......... A61B 17/43; A61B 2017/00876; A61B 2503/40; A61B 5/4325; A61D 19/027;
(Continued)

(56) References Cited

U.S. PATENT DOCUMENTS 3,507,281 A     4/1970 Cassou
2004/0199044 A1*   10/2004 Verberckmoes ..... A61D 19/027
                                                    600/35

FOREIGN PATENT DOCUMENTS

FR        1 472 139 A     3/1967
FR        2 705 880 A1    12/1994
(Continued)

OTHER PUBLICATIONS

Written Opinion of the French priority application FR1455079.

*Primary Examiner* — Imani N Hayman
(74) *Attorney, Agent, or Firm* — Young & Thompson (57) ABSTRACT

The invention concerns a device for the atraumatic transfer of a material or substance with a reproductive, therapeutic or diagnostic purpose into a female mammal, comprising a body assembly, an outer sheath suitable for being inserted as far as the start of one of the uterine horns, an inner sheath inside the outer sheath and capable of being extended into the uterine horn, and a piston inserted into the inner sheath order to push the material or substance up to the distal end of the inner sheath. The body assembly comprises a rod extending away from the outer sheath, and on which a shuttle assembly is slidingly mounted, comprising a primary shuttle, mounted sliding on said rod and to which the piston is attached, and a secondary shuttle, mounted sliding on said primary shuttle and to which the inner sheath is attached.

18 Claims, 4 Drawing Sheets

(51) Int. Cl.
  *A61B 5/00* (2006.01)
  *A61D 7/00* (2006.01)
  *A61D 19/04* (2006.01)
  *A61M 31/00* (2006.01)
  *A61B 17/00* (2006.01)

(52) U.S. Cl.
  CPC ............... *A61D 7/00* (2013.01); *A61D 19/04* (2013.01); *A61M 31/00* (2013.01); *A61B 2017/00876* (2013.01); *A61B 2503/40* (2013.01); *A61M 2205/0272* (2013.01); *A61M 2210/1433* (2013.01); *A61M 2250/00* (2013.01)

(58) Field of Classification Search
  CPC . A61D 19/04; A61D 7/00; A61M 2205/0272; A61M 2210/1433; A61M 2250/00; A61M 31/00
  See application file for complete search history.

(56) References Cited

FOREIGN PATENT DOCUMENTS

| | | |
|---|---|---|
| GB | 867 274 A | 5/1961 |
| WO | WO 03/065925 A1 | 8/2006 |

\* cited by examiner

DEVICE FOR THE ATRAUMATIC TRANSFER OF A MATERIAL OR SUBSTANCE WITH A REPRODUCTIVE, THERAPEUTIC OR DIAGNOSTIC PURPOSE INTO FEMALE MAMMALS

The present invention pertains the general field of the transfer, in vivo, of a material of substance with a reproductive, therapeutic or diagnostic purpose into an uterine horn of a female mammal, such as a bovine, and particularly relates to a device for such transfer, preferably into the upper part of an uterine horn.

The expression "material or substance with a reproductive purpose" (or reproduction) refers to semen or an embryo, wherein in such a case the transfer device is an artificial insemination device or an embryo transfer device. The reproduction material could be contained within a straw, as well known in the art.

The expression "material or substance with a therapeutic purpose" refers to any agent aiming to make the subject pass from a pathological state to a normal state, or to prevent a pathological state. Thus, deep intrauterine antibiotics, antiseptic solutions or isotonic wash solutions could be mentioned as examples.

The expression "material or substance with a diagnostic purpose" refers to any agent allowing or helping a physician to establish a diagnostic. Thus, marking substances such as methylene blue could be mentioned as examples.

Regarding the transfer of reproduction material, artificial insemination devices or embryo transfer devices are known, having a set of sheaths intended to slide with respect to each other, the most inner sheath comprising the reproduction material to be placed, and a plunger allowing to push said reproduction material out of the sheath.

Such a device is disclosed in patent FR 2705880. It comprises a flexible tip, attached to the proximal end of an elongated tube, with which it forms an inner sheath, the tip having a passage communicating with a straw engaged in the elongated tube. The front part of the tip has a conical shape so as to make it pass through the cervical canal of a female subject without damaging it, the flexible tip being thereafter moved within an uterine horn until reaching the upper part thereof. The device also comprises means for protecting against an exterior contamination, constituted by a first means enclosing the elongated tube and a second means surrounding the tip and the first means. A plunger is arranged in the elongated tube and a pressure thereon allows to send the content of the straw in the flexible tip, when the device is inserted within the vaginal canal of the subject.

However, the device according to patent FR 2705880 does not allow to expel the entire content of the straw. Indeed, the diameter of the plunger is larger than the inner diameter of the flexible tip. Thus, the plunger does not enter the latter, and the inner volume of the flexible tip, which is long enough to reach the upper part of the uterine horn, thus constitutes a significant dead volume. This problem would also exist in the case, not considered in patent FR 2705880, of the transfer of a material or substance with a therapeutic or diagnostic purpose.

Furthermore, it is necessary, when using any device for the transfer of a material or substance with a reproductive, therapeutic or diagnostic purpose, not to injure the animal. Indeed, for example in the case of artificial insemination, the trauma associated with an injury will cause a local inflammatory reaction which will be spermicide, thereby limiting the chances of success of the fertilization. Therefore, one should avoid that the device be likely, by the sizes thereof and/or the operation thereof, to injure the animal. In other words, the device must be atraumatic.

The present invention aims to overcome the drawbacks mentioned above and to provide a device for the atraumatic transfer of a material or substance with a reproductive, therapeutic or diagnostic purpose allowing to transfer the entire material or substance within the adequate region, for a better efficiency of the material or substance such as, for example, a better success rate of the artificial insemination or the embryo transfer, without any risk of injury of the animal.

The present invention relates to a device for the atraumatic transfer of a material or substance with a reproductive, therapeutic or diagnostic purpose into a female mammal, such as a bovine, allowing a transfer into a region, so-called transfer region, of an uterine horn of a female mammal, the device comprising:

a body assembly;

an outer sheath having an open proximal end and an open distal end, the outer sheath being integral with the body assembly and able to be inserted into the vagina of the female mammal and to pass the uterine cervix of the female mammal, preferably up to the entry of one of the two uterine horns;

an inner sheath having an open proximal end, a distal end in which at least one opening, so-called transfer opening, is provided, and an inner channel extending between the proximal and distal ends of the inner sheath and able to receive a material, or a substance, with a reproductive, therapeutic or diagnostic purpose to be transferred, the inner sheath being slidably received inside the outer sheath and being flexible so as to be able to be extended, from the distal end of the outer sheath, into the uterine horn of the female mammal until the distal end of the inner sheath is located in the transfer region; and a plunger intended, after placing inside the inner sheath the material or substance to be transferred, to be inserted into the inner sheath so as to be able to slide therein and to move, by a relative translation movement between the plunger and the inner sheath, the material or substance to be transferred towards the distal end of the inner sheath, through which the material or substance to be transferred will be placed in the transfer region, the device being characterized in that a part, so-called distal part, of the plunger is flexible and able to be extended into the part, so-called distal part, of the inner sheath which is intended to be extended into the uterine horn, and in that the device has joint movement means for jointly moving the inner sheath and the plunger to the transfer region, with said distal part of the plunger located inside said distal part of the inner sheath, and retraction means for retracting the inner sheath on the plunger at the transfer region, so as to force out the material or substance to be transferred through the distal end of the inner sheath, under the thrust of the plunger.

The expression "joint movement" means a simultaneous movement of the inner sheath and the plunger, without any relative movement between the inner sheath and the plunger. Thus, the joint movement of the inner sheath and of the plunger, which consists in extending the distal part of the inner sheath into an uterine horn, does not cause placing of the material or substance to be transferred.

The retraction movement of the inner sheath on the distal part of the plunger allows to force out the material or substance to be transferred while preventing an injury of the animal, as the exit of the material or substance to be transferred is no longer obtained by a thrust movement of the plunger towards the upper part of the uterine horn. The transfer of the material or substance is thus atraumatic.

In addition, the problem of dead volume is solved in that the distal part of the plunger extends into the part of the inner sheath which extends into the uterine horn.

According to a preferred embodiment of the present invention, the body assembly comprises a shaft extending in the direction away from the outer sheath and on which is slidably mounted a shuttle assembly which comprises a primary shuttle, slidably mounted on said rod and to which the plunger is attached, and a secondary shuttle, slidably mounted on said primary shuttle and to which the proximal end of the inner sheath is attached, the primary shuttle and the secondary shuttle constituting said joint movement means and said retraction means.

The inner sheath can thus be moved forward inside the uterine horn without any relative movement with respect to the plunger, by moving the primary shuttle towards the outer sheath with the secondary shuttle stationary with respect to the primary shuttle, then, after the distal end of the inner sheath has reached the transfer region, the inner sheath can be retracted on the plunger by sliding the secondary shuttle away from the outer sheath while the plunger remains stationary with respect to the outer sheath or is moved forward, jointly with the inner sheath, by sliding the primary shuttle towards the outer sheath.

Preferably, the inner sheath may comprise a proximal part, inside the outer sheath, and the flexible distal part, preferably with a length greater than 130 mm, more preferably a length of 255.5 mm, intended to be extended into the uterine horn, the proximal part being less flexible than the distal part.

Providing such a minimum length allows the distal end of the inner sheath to go deep enough inside an uterine horn for a good reproductive, therapeutic or diagnostic effect and, in the case of the preferred length of 255.5 mm, to reach the upper part of an uterine horn for a better effect. Thus, in the case where the device is used as an artificial insemination device, the semen can be placed close to the spermatic tank, for an improved success rate.

According to a particular embodiment of the device according to the present invention, suitable for the transfer of a material or substance with a reproductive, therapeutic or diagnostic purpose contained inside the inner space, with a given cross-section, of a straw, the inner channel of the inner sheath is able to receive such a straw, the plunger is able to pass through the straw to force out the material or substance to be transferred and the inner sheath comprises translation stopping means for stopping the translation of the straw in the direction of the distal end, the translation stopping means for stopping translation of the straw being formed, for example, by an inner shoulder in the inner sheath, if appropriate located at the junction between the proximal and distal parts of the inner sheath and, preferably, centered on the axis of the inner sheath.

Preferably, when the device according to the present invention comprises the translation stopping means formed by an inner shoulder and is for use with a straw the inner space of which has a cross-section equal to the passage cross-section of the inner channel at the inner shoulder, advantageously there are centering means for centering the straw on the axis of the inner sheath when the straw is abutted against the translation stopping means, said centering means being formed, for example, by a narrowing of the passage cross-section of the inner channel of the inner sheath at the vicinity of the shoulder, on the proximal end side of the inner sheath, the narrowing being centered on the axis of the inner sheath.

The body assembly may comprise a nose in which are provided a through passage, from an end of which extends the outer sheath, on a first side of the nose, and a through hole opening onto a second side of the nose, opposite said first side, and from which extends the shaft of the body assembly, the axis of the through passage and the axis of the hole being parallel and coplanar.

The outer sheath may be connected to the nose by a connector, such as of the Luer type.

The secondary shuttle may comprise a through passage for the plunger, and the inner sheath may be connected to the secondary shuttle by a connector, such as of the Luer type.

Preferably, the distal ends of the outer sheath and of the inner sheath are free of sharp edges and ridges, said distal ends being preferably rounded so as to facilitate moving forward the outer and inner sheathes inside the mammal without injuring the mammal.

The distal end of the inner sheath may be formed by a tip having two lateral outlets allowing to place in the transfer region the material or substance to be transferred, such as semen towards the spermatic crypts, said tip having preferably a rounded shape at the end thereof.

The distal end of the outer sheath may be formed by a tip made of flexible material, with a warhead shape and having a pierced cross-shaped opening.

The inner and outer sheathes may be made of plastic material.

The device according to the present invention advantageously comprises a sanitary jacket, which surrounds the outer sheath and is attached on the end of the outer sheath, said sanitary jacket allowing to keep the device clean until it enters the uterine cervix, said sanitary jacket being able to be pierced so as to allow the extension of the inner sheath from the outer sheath. The sanitary jacket could be of the type described in the European patent application EP0093630.

The plunger may be formed by a combination of a rod, for example made of metal, and a wire, respectively on the proximal side and the distal side of the device, the wire forming the distal part of the plunger intended to be extended into the part of the inner sheath intended to be extended into the uterine horn of the mammal.

As an alternative, the plunger may be formed by a rigid stem, forming the proximal part of the plunger with which it is attached, if appropriate, to the primary shuttle, by a rod which is flexible and able to pass through the straw, the rod, which is for example made of metal, extending from a distal end of the stem, and by a wire extending from a distal end of the rod, the wire and the distal end region of the rod forming the distal part of the plunger intended to be extended into the part of the inner sheath intended to be extended into the uterine horn of the mammal.

The length of the plunger may be substantially equal to that of the inner sheath.

According to a particular embodiment, the secondary shuttle is provided with a first magnet, the primary shuttle is provided, in the distal end region thereof, with a second magnet, and the shaft is provided with a third magnet in the proximal end region thereof, the magnets being configured so as to be able to be aligned with each other in a given position of the primary and secondary shuttles and attract each other so as to hold in position the primary and secondary shuttles with respect to the shaft.

Preferably, the shaft carries, at the distal end thereof, a stop, preferably a stop received within a through hole of the primary shuttle, by which the primary shuttle is slidably mounted on the shaft, the through hole comprising, preferably at the distal end thereof, a shoulder having a stopping surface for said stop.

Also disclosed herein is a method for the transfer of a material or substance with a reproductive, therapeutic or diagnostic purpose within a region, called transfer region, of an uterine horn of a female mammal, such as a bovine, preferably at the upper part of the uterine horn, at proximity of the spermatic tank, using a transfer device as defined above, characterized in that is comprises the following steps:

inserting a material or substance with a reproductive, therapeutic or diagnostic purpose to be transferred, inside the inner sheath through the proximal end of the latter, the inner sheath being located inside the outer sheath;

inserting the plunger inside the inner sheath and, in the case of the use of a straw of material or substance to be transferred, pushing the straw until it is stopped by the translation stopping means, and then piercing the straw by the plunger, such that the plunger pushes towards the distal end of the inner sheath the material or substance to be transferred;

attaching a head of the plunger to the primary shuttle, the primary shuttle being at the proximal end of the shaft;

inserting the outer sheath into the vagina of a female mammal, until the distal end of the outer sheath passes the uterine cervix and is oriented towards one of the two uterine horns, while at the same time tearing the sanitary jacket if it is present;

moving the shuttle assembly towards the outer sheath, so as to insert the inner sheath into the uterine horn until the distal end of the inner sheath is in the transfer region;

continuing to move the shuttle assembly towards the outer sheath while moving the secondary shuttle, with respect to the primary shuttle, away from the outer sheath, so as to retract the inner sheath into the outer sheath and thus allow the material or substance to be transferred, to be forced out the distal end of the inner sheath and be placed in the transfer region; and removing the device from the female mammal.

In order to better illustrate the subject-matter of the present invention, two particular embodiments will now be described, for information and non-limiting purposes, with reference to the appended drawings.

Figures 1, 2:
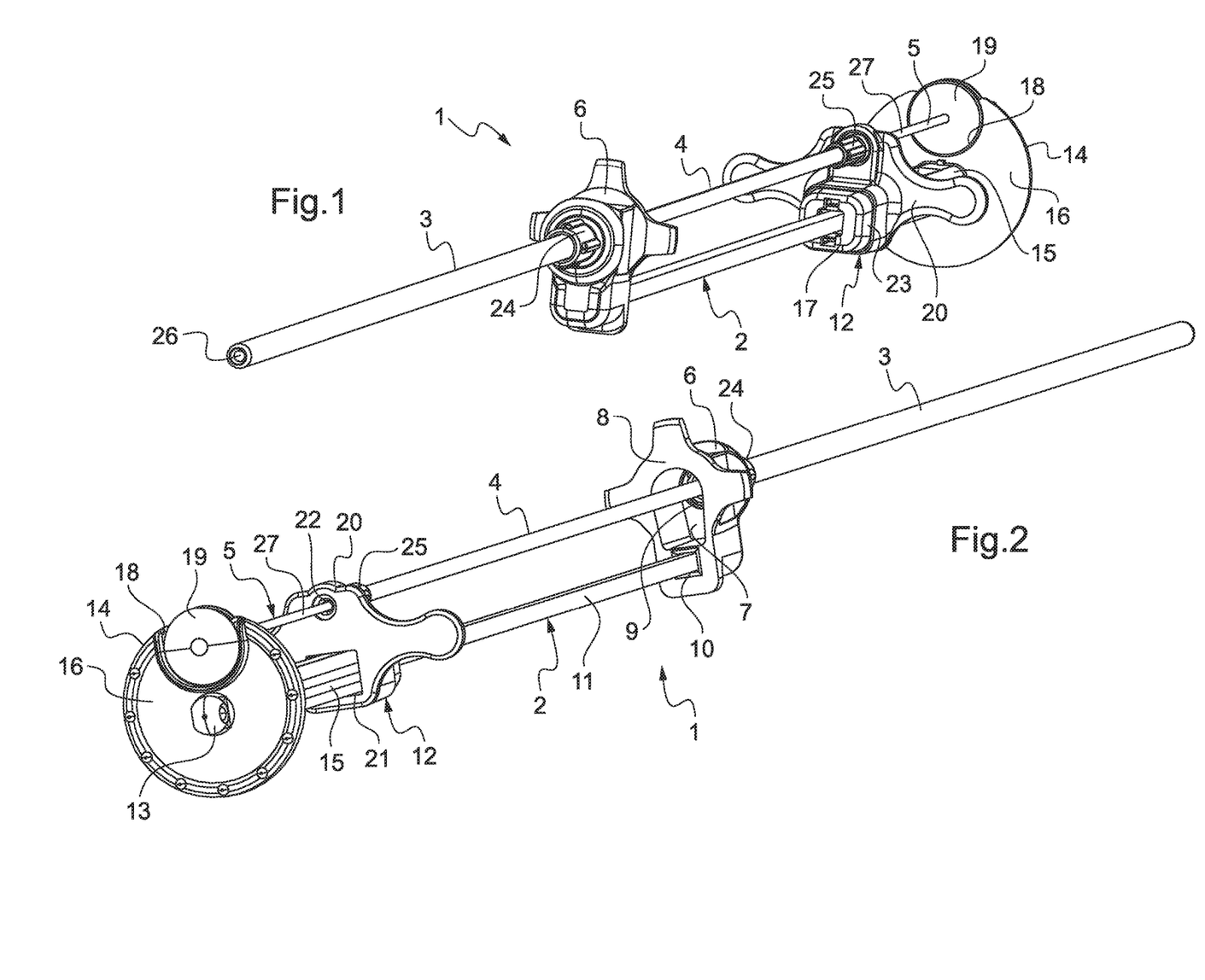
FIGS. 1 and 2 are perspective views, respectively on the distal side and the proximal side of the artificial insemination or embryo transfer device according to a first embodiment of the present invention, in the position of insertion into the animal.

If referring to FIGS. 1 and 2, a transfer device 1 according to the present invention is shown in its position of insertion into the animal, which device comprises a body assembly 2, an outer sheath 3, an inner sheath 4 and a plunger 5.

In the example shown, the device 1 is used with a straw of semen and thus constitutes an artificial insemination device. However, this device 1 can be used for the transfer of another material or substance with a reproductive, therapeutic or diagnostic purpose.

The body assembly 2 comprises a nose 6 shaped as a substantially parallelepiped body, having a recess 7 on one of the two largest faces 8 thereof, at the bottom of which is formed a through hole 9, said face 8 being oriented towards the proximal side of the device, and having a blind hole 10 formed on this same large face 8 and in which a shaft 11 is attached. The axis of the shaft 11 is parallel and coplanar with the axis of the outer sheath 3.

The body assembly 2 also comprises a shuttle assembly 12 slidably mounted on said shift 11. The shaft 11 has a rectangular section, whereby the shuttle assembly 12 cannot pivot around the longitudinal axis of the shaft 11.

The shaft 11 further comprises a translation stop 13 at the proximal end of the shaft 11, so as to prevent the shuttle assembly 12 to be separated from the shaft 11.

The shuttle assembly 12 comprises a primary shuttle 14 formed by a longitudinal part 15, with a rectangular cross-section, and a disk-shaped proximal part 16, and has a longitudinal through hole 17 the cross-section of which substantially corresponds to the cross-section of the shaft 11. The disk-shaped proximal part 16 comprises a notch 18 receiving the head 19 of the plunger 5.

The shuttle assembly 12 also comprises a secondary shuttle 20 slidably mounted on the longitudinal part 15 of the primary shuttle 14, via a first through hole 21 the cross-section of which substantially corresponds to the outer cross-section of the longitudinal part 15 of the primary shuttle 14, whereby the secondary shuttle 20 cannot pivot around the longitudinal axis of the primary shuttle 14.

The secondary shuttle 20 further comprises a second through hole 22 through which passes the plunger 5.

The shuttle assembly 12 also comprises a blocking ring 23 attached to the distal end of the primary shuttle and limiting the sliding movement of the secondary shuttle 20 with respect to the primary shuttle 14.

The outer sheath 3 is connected to the body 6 of the body assembly 2 by a first Luer connector 24 at the through hole 9 of the nose 6, such that the outer sheath 3 and said through hole 9 of the nose 6 communicate with each other.

The inner sheath 4 is inserted into the outer sheath 3 and connected by a Luer connector 25 to the secondary shuttle 20 at the second through hole 22 thereof, such that the inner sheath 4 and said second through hole 22 communicate with each other. The inner sheath 4 further comprises an end tip 26.

The plunger 5 comprises a plunger body 27 inserted into the inner sheath 4. The plunger 5 is, in this position of insertion into the animal, integral with the primary shuttle 14, such that a translation movement of the primary shuttle 14 allows to jointly move the plunger 5 in translation.

The operation of the device according to the particular embodiment will now be described in more detail, with reference to FIGS. 3 to 6.

Figures 3, 4:
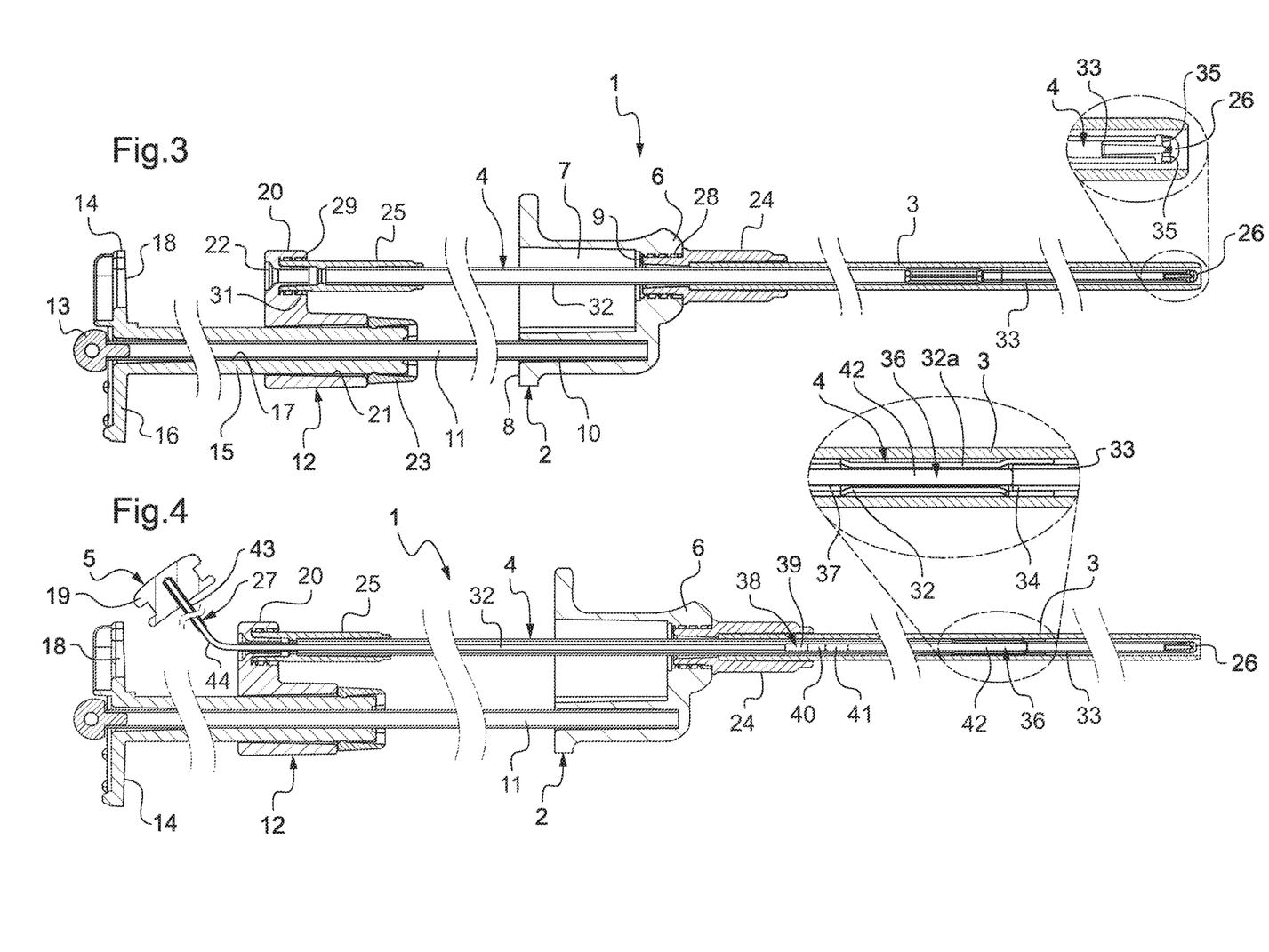
FIG. 3 is a longitudinal cross-sectional view of the device according to the first embodiment, before the position of insertion into the animal, the inner and outer sheathes having been placed on the body assembly, with a detailed view of the distal ends of the inner and outer sheathes.
FIG. 4 is a longitudinal cross-sectional view of the device according to the first embodiment, before the position of insertion into the animal, a straw of semen having been inserted into the inner sheath and a plunger having been inserted into the inner sheath after the straw, with a detailed view of the stopping shoulder and the centering narrowing of the straw.

Before use, an operator grips the device 1 which at that time comprises the body assembly 2, and places it on a jig (not shown). The operator places outer 3 and inner 4 sheathes enclosed within an outer sanitary jacket (not shown), which surrounds the circumferential longitudinal surface of the outer sheath 3 and also the distal end thereof. The sanitary jacket enclosing the sheathes 3,4 is attached on the nose 6 and allows to keep the device 1 clean until it enters the uterine cervix. For example, the sanitary jacket could be made of plastic material, such as polyethylene.

After having passed the outer 3 and inner 4 sheathes through the through hole 9, from the distal side of the nose 6, the sanitary jacket being then attached on a tooth carried by the nose 6, the Luer connector 24 is screwed on the body assembly 2 and connects the outer sheath 3 to the body assembly 2, the distal part of said Luer connector 24 having a screw thread 28 and the through hole 9 of the body 6 having a corresponding screw thread.

Then, the operator connects the inner sheath 4 to the secondary shuttle 20 by screwing the Luer connector 25 to the latter, the distal part of said Luer connector 25 having a screw thread 29 and the distal side of the secondary shuttle 30 having a recess 31 concentric with the through hole 22 and comprising a screw thread corresponding to the screw thread 29 on the side wall of said recess 31, so as to obtain the device in the configuration shown in FIG. 3.

As it can be better seen in FIG. 3, the inner sheath 4 is in fact made of two parts, namely a proximal part 32 and a distal part 33, wherein the distal part 33, which is intended to be extended into the uterine horn of an animal, is flexible so as not to injure the animal, while the proximal part 32, which remains inside the outer sheath 3, may be made of a less flexible material. Thus, the distal part 33 could be made of a mixture of low-density polyethylene and high-density polyethylene, while the proximal part 32 could be made of polycarbonate.

As it can be seen in the detailed view of FIG. 3, the tip 26 which closes the distal end of the inner sheath 4 has two outlet ports 35, so-called transfer openings, disposed perpendicularly to the longitudinal axis of the inner sheath 4.

Then, as it can be seen in FIG. 4, the operator inserts into the inner sheath 4 a straw 36 of semen, after preparing the latter as well known in the art (thawing, etc), and then inserts the plunger 5 into said inner sheath and pushes the plunger 5 such that the straw 36 is abutted against means for stopping the translation of the straw 36.

As it can be seen in the detailed view of the FIG. 4, the stopping means are formed by an inner shoulder 34 formed by the end face of the distal part 33, on the proximal side, since the passage cross-section of the distal part 33 is smaller than the passage cross-section of the proximal part 32, said proximal 32 and distal 33 parts being coaxial. At the vicinity of the inner shoulder 34 is provided a reduction of cross-section, or narrowing, 32a, of the proximal part 32, centered on the longitudinal axis of the inner sheath 4 and which is for centering the straw 36 such that the inner space thereof is directly facing the inner channel of the distal part 33, so as to allow the passage of the semen of the straw 36 to the distal part 33.

The straw 36, well known in itself, is formed by a tube 37 in which, from the proximal side to the distal side thereof, are provided respectively a plug 38 formed by a first piece of cotton 39, by a polyvinyl alcohol (PVA) part 40 and by a second piece of cotton 41, and the semen to be placed 42.

The straw 36 is closed by fusion sealing at the distal end thereof, and the plug 38 closes the other end.

The plunger body 27 of the plunger 5 is formed by a metal rod 43 and a wire 44, the proximal end of the wire 44 being made integral with the rod 43 by any suitable means, for example by welding and bonding. The diameter of the wire 44 is smaller than the inner diameter of the tube 37 of the straw 36.

Figure 5:
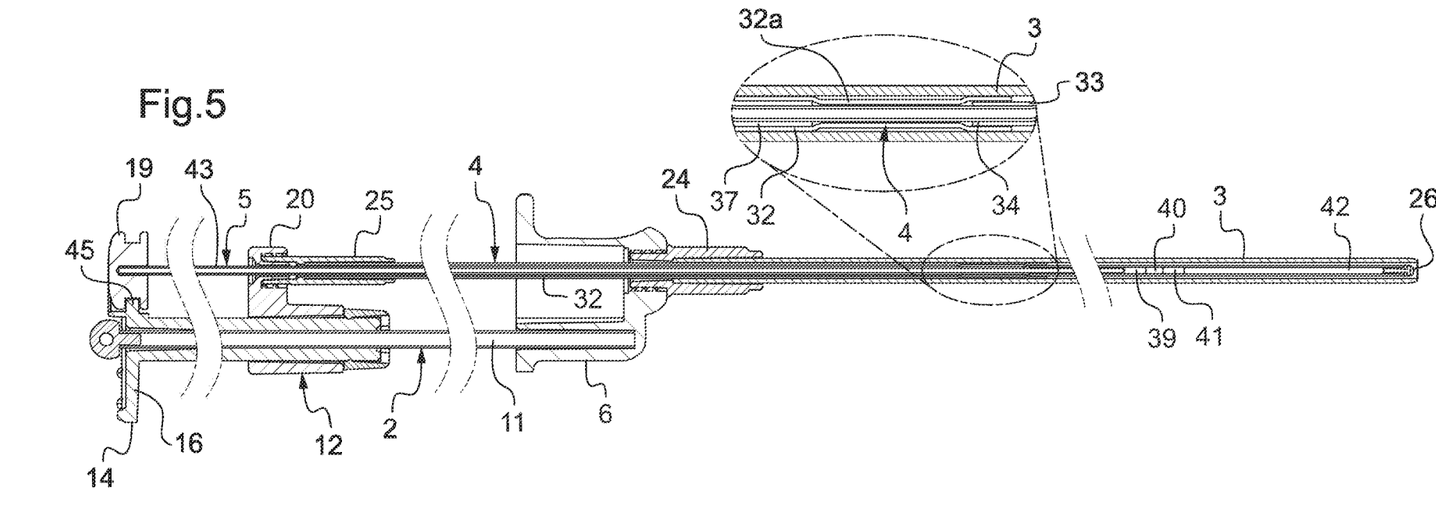
FIG. 5 is a longitudinal cross-sectional view of the device according to the first embodiment, in its position of insertion into the animal such as shown in FIGS. 1 and 2, the plunger having pushed the content of the straw of semen towards the distal end of the device, with a detailed view similar to that of FIG. 4.

Then, as it can be seen in FIG. 5, the operator pushes the plunger 5 in the distal direction of the inner sheath 4 with respect to its position in FIG. 4.

Moving forward the plunger 5 allowed the wire 44, due to the sufficient rigidity offered by the rod 43, to push the plug 38 of the straw 36, and thus to push the content thereof towards the distal end of the inner sheath 4, the tube 37 of the straw 36 being held in place by the stopping means 34.

The plunger 5 is moved forward by the operator to a position in which it is arranged parallel to the shaft 11 and in which the plunger head 19 is inserted into the notch 18 of the proximal part 16 of the primary shuttle 14.

Means 45 for locking in position the plunger 5, by form fitting, are provided inside said notch 18, so as to make the primary shuttle 14 and the plunger 5 integral in translation.

The length of the plunger 5 is selected such that, in the position in FIG. 5, a gap is formed in the distal end of the inner sheath 4, between the distal end of the plunger 5 and the end tip 26 of the inner sheath 4, and such that said gap can hold the content of the straw 36 (plug 38 and semen 42) without the semen 42 flowing by the ports 35 of the tip 26.

The following features can be mentioned:
  outer sheath: length of 443 mm, outer diameter of 5.9 mm and inner diameter of 3.8 mm;
  inner sheath: length of 799.5 mm, outer diameter of 3.65 mm and inner diameter of 2.65 mm for the proximal part upstream the narrowing, inner diameter of 2.5 mm at the narrowing, and outer diameter of 2.5 mm and inner diameter of 1.6 mm for the distal part;
  plunger: length of the metal rod of 386 mm, length of the wire of 390 mm, diameter of the wire of 1.25 mm.

According to FIG. 5, one will understand that the movements of the different elements of the shuttle assembly 12 allow to obtain, from the position seen in said FIG. 5, different movements of the elements of the device 1, namely:
  a movement of the shuttle assembly 12 towards the distal side of the device 1 allows to move the inner sheath 4, its content and the plunger 5 towards the distal side of the device 1, so as to cause the inner sheath 4, with the wire 44 therein, to exit through the distal end of the outer sheath 3; and
  a movement of the secondary shuttle towards the proximal side of the device 1 allows to move the inner sheath 4 alone towards the proximal side of the device, and to force out the semen 42 through the ports 35, the plunger 5 remaining stationary, the action of moving the inner sheath 4 on the stationary plunger 5 then exerting as a thrust from the plunger 5 towards the distal side.

Thus, in order to place the semen 42, after having identified the ovulatory side, the operator inserts the distal end of the device 1, in the position in FIG. 5, into the vagina of the animal.

The diameter and the material of the outer sheath 3 are selected in order to allow it to easily pass through the uterine cervix of the animal without injuring the animal, and the length thereof is selected such that the distal end thereof can reach the entry of one of the two uterine horns of the animal. The operator tears the sanitary jacket at the entry of the uterine cervix.

Once the distal end of the outer sheath 3 is in position at the entry of an uterine horn, the operator pushes, with one hand, the shuttle assembly 12 so as to force out the inner sheath 4 until the distal end of the inner sheath 4 reaches the adequate transfer region, namely the upper part of the uterine horn, at proximity of the spermatic tank, the operator guiding and controlling, with his/her other hand, by passing through the rectum of the animal, the movement of the inner sheath 4 inside the uterine horn.

At this time, the secondary shuttle 20 is not moved with respect to the primary shuttle 14, such that no relative movement between the inner sheath 4 and the plunger 5 occurs.

It should be noted that, during this phase, the plug 38 already surrounds the distal end of the wire 45 and thus protects the animal against the end of the plunger 5 during the movement forward of the flexible sheath 4 and plunger 5 inside the uterine horn.

The operator then pulls the secondary shuttle 20 towards the proximal side of the device 1 with his/her free hand, with his/her thumb against the disk-shaped proximal part 16 and his/her other fingers pushing on the secondary shuttle 20, or vice versa, just as with a syringe. The inner sheath 4 is thus retracted on the plunger 5 and the semen 42 is pushed out of the inner sheath 4 through the ports 35 so as to be placed in the animal.

Figure 6:
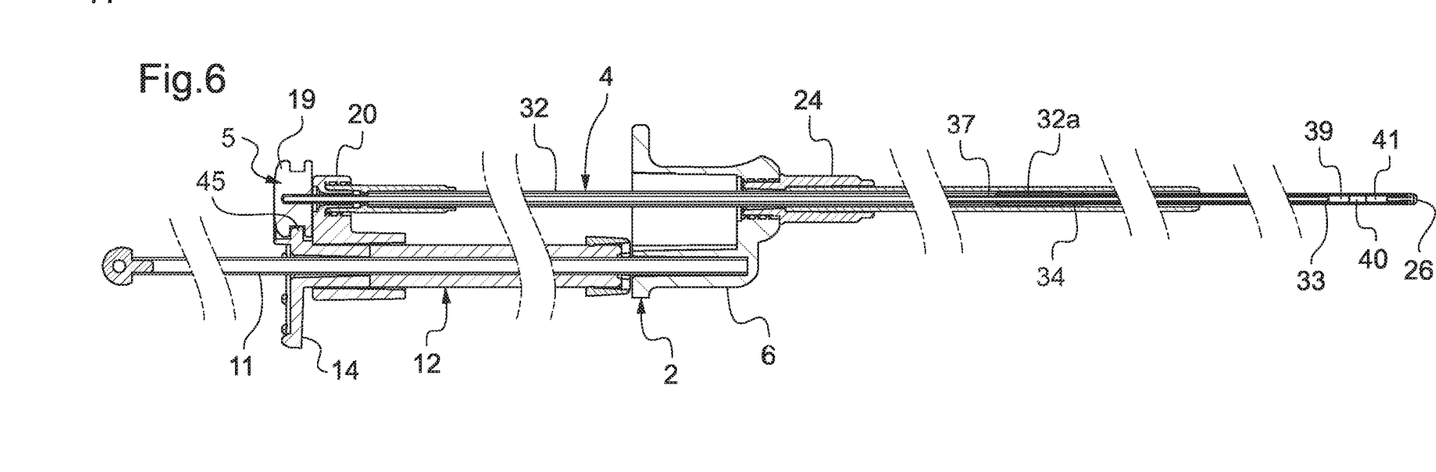
FIG. 6 is a longitudinal cross-sectional view of the device according to the first embodiment, in its position after placing the semen inside the animal.

At the end of the transfer operation, the device 1 can be, according to the anatomy of the animal, in the position shown in FIG. 6, on which it can be noted that the shuttle assembly 12 has been moved towards the distal side of the device 1 until abutting against the body 6 of the body assembly 2 and that the secondary shuttle 20 has been moved towards the proximal side of the primary shuttle 14 until abutting against it.

In this position, it can be noted that the distal part 33 of the inner sheath 4 is mostly located outside the outer sheath 3, and that the semen 42 has been pushed out of the device 1 through the two ports 35, the plug 38 of the straw 36 remaining inside the distal tip 26 of the inner sheath 4.

It can thus be noted that the device according to the present invention allows to place in the adequate region almost the entire material or substance to be transferred, for a better transfer effect, such as a better success rate for the artificial insemination or the embryo transfer, without any risk of injury of the animal.

Figure 7:
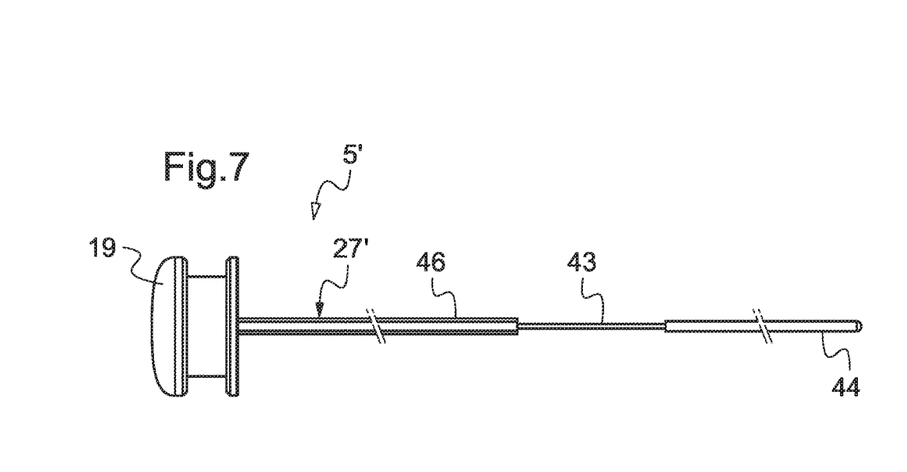
FIG. 7 is a profile view of the plunger according to an alternative embodiment.

If now referring to FIG. 7, an alternative of the plunger, designated by the reference number 5', has been shown, the body 27' of which has a rigid part 46, here formed by a stainless steel stem at the distal end of which the proximal end of the rod 43 is attached. The wire 44 extends from the distal end of the rod 43. The diameter of the rod 43 is selected to be smaller than or equal to the diameter of the wire 44, such that the rod 43, on one hand, can also pass through the straw 36 and, on the other hand, is more flexible than in the first embodiment and, therefore, can also be extended into the distal part 33 of the inner sheath 4. The stem constitutes a means for stiffening the proximal part of the plunger 5' and thus ensuring the thrust of the plunger 5' inside the inner sheath 4. In other words, the body 27' of the plunger 5' has a flexible distal part, formed by the wire 44, a middle part also flexible, formed by the rod 43 and passing through the straw 36, and a rigid proximal part 46.

In this alternative:
 the exposed length of the metal rod 43 is 120.3 mm and the diameter thereof is 1.2 mm;
 the length of the stem 46 is 332.3 mm, the outer diameter thereof is 2 mm; and
 the length of the wire 44 is 265 mm and the diameter thereof is 1.25 mm.

For the sheathes, an outer sheath with a length of 423 mm and an inner sheath with a length of 726 mm could be used, the other features of the sheathes mentioned in relation to the first embodiment remaining unchanged.

This particular arrangement of the plunger 5' allows to stiffen the latter, thereby preventing it from bending and facilitating the discharge of the semen.

Figure 8:
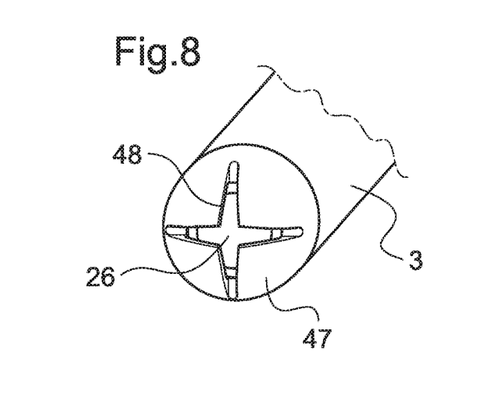
FIG. 8 is a perspective view of the distal end of the outer sheath according to an alternative embodiment.

Obviously, for a result similar to the alternative described above, in the first embodiment, a metal rod 43 with a smaller diameter could be provided, such that it can pass through the straw, but the proximal part of which would be stiffened, for example by being embedded in a rigid tube. If now referring to FIG. 8, it can be seen that the distal end of the outer sheath 3 comprises, according to an alternative embodiment, a tip 47 with a warhead shape and made of flexible material, such as an elastomer, pierced with a cross-shaped opening 48. The diameter of the tip is strictly identical to that of the outer sheath 3. Such a shape allows to further improve the atraumatic property of the device and further protect the end tip 26 of the inner sheath 4.

Figure 9:
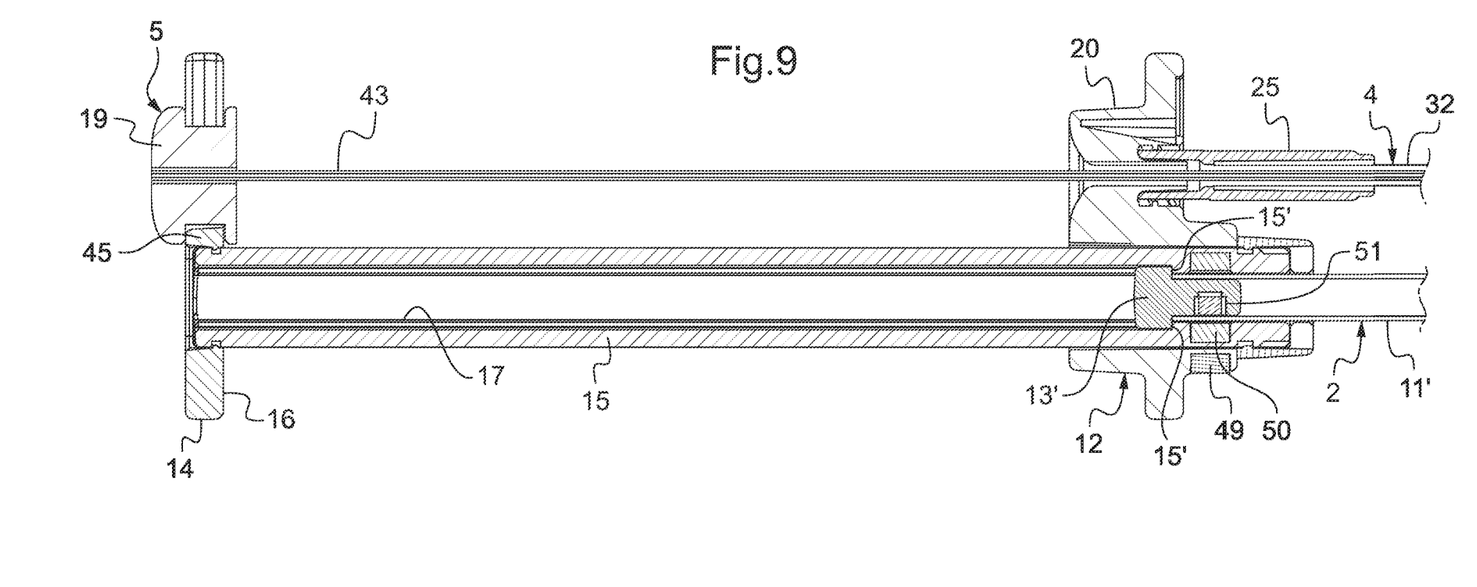
FIG. 9 is a longitudinal cross-sectional view of the distal part of the device according to a second particular embodiment of the present invention.

If finally referring to FIG. 9, showing a second particular embodiment of the present invention, it can be seen that the secondary shuttle 20 is provided with a first magnet 49, the longitudinal part 15 of the primary shuttle 14 is provided, at the distal end thereof, with a second magnet 50, and the shaft 11' comprises a stop 13' provided with a third magnet 51.

The shaft 11' is shorter than the shaft 11, and the stop 13' is able to enter in the longitudinal part 15. The stop 13' abuts against a shoulder 15' formed in the through hole 17 of the longitudinal part 15. This allows to provide a device even more compact.

The magnets 49, 50, 51 are arranged with their poles such that, when their centers are substantially aligned on a same line, namely in the position before the insertion into the animal, as shown in FIG. 9, the second magnet 50 attracts the first and third magnets 49 and 51.

Thus, the device elements are held in position when, for example, the operator handles the apparatus before the artificial insemination.

This allows to avoid an unintentional movement of the device elements, which unintentional movement could cause the ejection of the content of the straw 33 out of the device.

In addition, temporary holding in position the primary 14 and secondary 20 shuttles by magnets provides a smooth operation of the shuttles: the shuttles 14 and 20 are not moved in a sudden manner at the beginning of their movement.

Of course, the embodiment described above of the present invention is for information and non-limiting purposes, and modifications could be made without departing from the scope of the present invention.

For example, it could be possible for the structure of the body assembly to be changed and, for example, not to use a nose as described above, or to add a graduation on the shaft 11, so as to allow the operator to know the distance at which the reproduction material has been placed, in the case where the shuttle assembly 12 has been moved in the proximal direction of the device 1 during the operation of transfer itself.

The invention claimed is:

1. A device for an atraumatic transfer of a material or substance with a reproductive, therapeutic, or diagnostic purpose into a transfer region of an uterine horn of a female bovine mammal, the device comprising:
a body assembly;
an outer sheath having an open proximal end and an open distal end, the outer sheath being integral with the body assembly and insertable into a vagina past a uterine cervix of the female bovine mammal;
an inner sheath having an open proximal end, a distal end in which at least one transfer opening is provided, and an inner channel extending between the open proximal end and the distal ends of the inner sheath and able to receive the material or substance with the reproductive, therapeutic, or diagnostic purpose, the inner sheath being slidably received inside the outer sheath and being flexible so as to be able to be extended, from the distal end of the outer sheath, into the uterine horn of the female bovine mammal until the distal end of the inner sheath is located in the transfer region; and
a plunger that is insertable, after placing the material or substance with the reproductive, therapeutic, or diagnostic purpose inside the inner sheath, into the inner sheath so as to be able to slide therein and to move, by a relative translation movement between the plunger and the inner sheath, the material or substance with the reproductive, therapeutic, or diagnostic purpose towards the distal end of the inner sheath, through which the material or substance with the reproductive, therapeutic, or diagnostic purpose is placed in the transfer region,
wherein a distal part of the plunger is flexible and able to be extended into the uterine horn through one of the at least one transfer opening on the distal end of the inner sheath,
wherein the device comprises a joint movement assembly for jointly moving the inner sheath and the plunger to the transfer region, with said distal part of the plunger located inside the inner sheath, and a retraction assembly for retracting the inner sheath on the plunger at the transfer region, so as to force out the material or substance with the reproductive, therapeutic, or diagnostic purpose through the distal end of the inner sheath, under a thrust of the plunger, and
wherein the body assembly comprises a shaft extending in a direction away from the outer sheath and on which is slidably mounted a shuttle assembly which comprises a primary shuttle, slidably mounted on said shaft and to which the plunger is attached, and a secondary shuttle, slidably mounted on said primary shuttle and to which the proximal end of the inner sheath is attached, the primary shuttle and the secondary shuttle constituting said joint movement assembly and said retraction assembly.

2. The device according to claim 1, wherein the inner sheath comprises a proximal part, inside the outer sheath, and a flexible distal part for extending into the uterine horn, the proximal part being less flexible than the distal part.

3. The device according to claim 2, wherein the flexible distal part has a length greater than 130 mm.

4. The device according to claim 2, wherein the flexible distal part has a length of 255.5 mm.

5. The device according to claim 1,
wherein the inner channel of the inner sheath is adapted to receive a straw with a given cross-section, the straw being configured to contain the material or substance with the reproductive, therapeutic or diagnostic purpose, and
wherein the plunger is adapted to pass through the straw to force out the material or substance with the reproductive, therapeutic or diagnostic purpose, and the inner sheath comprises a translation stopper for stopping a translation of the straw in a direction of the distal end.

6. The device according to claim 5,
wherein the translation stopper is formed by an inner shoulder in the inner sheath,
wherein the cross-section of the inner space of the straw is equal to a passage cross-section of the inner channel at the inner shoulder, and
wherein a centering structure is provided for centering the straw on an axis of the inner sheath when the straw is abutted against the translation stopper.

7. The device according to claim 6, wherein said centering structure is formed by a narrowing of the passage cross-section of the inner channel of the inner sheath at a vicinity of the inner shoulder, on a proximal end side of the inner sheath, the narrowing being centered on the axis of the inner sheath.

8. The device according to claim 1, wherein the body assembly comprises a nose in which is provided a through passage, from an end of which extends the outer sheath, on a first side of the nose, and a through hole opening onto a second side of the nose, opposite said first side, and from which extends the shaft of the body assembly, the axis of the through passage and the axis of the through hole opening being parallel and coplanar.

9. The device according to claim 1, wherein the secondary shuttle comprises a through passage for the plunger, and wherein the inner sheath is connected to the secondary shuttle by a connector.

10. The device according to claim 1, wherein the distal end of the outer sheath and the distal end of the inner sheath are free of sharp edges and ridges.

11. The device according to claim 10, wherein the distal end of the outer sheath and the distal end of the inner sheath are rounded so as to facilitate moving forward the outer sheath and the inner sheathes inside the bovine mammal without injuring the bovine mammal.

12. The device according to claim 1, wherein the distal end of the inner sheath is formed by a tip having two lateral outlets allowing to place the material or substance with the reproductive, therapeutic or diagnostic purpose in the transfer region.

13. The device according to claim 12, wherein the tip forming the distal end of the inner sheath has a rounded shape at an end of the tip.

14. The device according to claim 1, wherein the distal end of the outer sheath is formed by a tip made of flexible material, with a warhead shape and having a pierced cross-shaped opening.

15. The device according to claim 1, wherein the plunger is formed by a combination of a rod and a wire, respectively on a proximal side and a distal side of the device, the wire forming the distal part of the plunger adapted to be extended into a part of the inner sheath that is adapted to be extend into the uterine horn of the bovine mammal.

16. The device according to claim 1, wherein a length of the plunger is substantially equal to a length of the inner sheath.

17. The device according to claim 1, wherein the secondary shuttle is provided with a first magnet, the primary shuttle is provided, in the distal end region thereof, with a second magnet, and the shaft is provided with a third magnet in the proximal end region thereof, the magnets being configured so as to be able to be aligned with each other in a given position of the primary and secondary shuttles and attract each other so as to hold in position the primary and secondary shuttles with respect to the shaft.

18. The device according to claim 1, wherein the shaft carries, at the distal end thereof, a stop received in a through hole of the primary shuttle, by which the primary shuttle is slidably mounted on the shaft, the through hole comprising a shoulder having a stopping surface for said stop.

* * * * *